(12) United States Patent
Rostaing et al.

(10) Patent No.: US 10,067,053 B2
(45) Date of Patent: Sep. 4, 2018

(54) TERAHERTZ IMAGE SENSOR

(71) Applicant: Commissariat à l'Énergie Atomique et aux Énergies Alternatives, Paris (FR)

(72) Inventors: Jean-Pierre Rostaing, La Côte Saint Andre (FR); Anaïs Mollard, Grenoble (FR)

(73) Assignee: Commissariat à l'Énergie Atomique et aux Énergies Alternatives, Paris (FR)

( * ) Notice: Subject to any disclaimer, the term of this patent is extended or adjusted under 35 U.S.C. 154(b) by 0 days.

(21) Appl. No.: 14/916,978

(22) PCT Filed: Sep. 15, 2014

(86) PCT No.: PCT/FR2014/052292
§ 371 (c)(1),
(2) Date: Mar. 4, 2016

(87) PCT Pub. No.: WO2015/040316
PCT Pub. Date: Mar. 26, 2015

(65) Prior Publication Data
US 2016/0216202 A1      Jul. 28, 2016

(30) Foreign Application Priority Data
Sep. 17, 2013    (FR) ..................... 13 58918

(51) Int. Cl.
*G01J 5/02*       (2006.01)
*G01N 21/3581*    (2014.01)
(Continued)

(52) U.S. Cl.
CPC ............ *G01N 21/3581* (2013.01); *G01S 7/03* (2013.01); *G01S 7/4914* (2013.01); *G01S 13/89* (2013.01);
(Continued)

(58) Field of Classification Search
CPC ........ G01J 5/20; G01J 5/08; G01J 5/16; G01J 5/12; H04N 5/33
See application file for complete search history.

(56) References Cited

U.S. PATENT DOCUMENTS 3,526,858 A    9/1970    Heinlein et al.
4,319,207 A    3/1982    Gignoux
(Continued)

OTHER PUBLICATIONS

Written Opinion, dated Dec. 1, 2014, from corresponding International Application No. PCT/FR2014/052292.
(Continued)

*Primary Examiner* — David Porta
*Assistant Examiner* — Mamadou Faye
(74) *Attorney, Agent, or Firm* — Wolf, Greenfield & Sacks, P.C.

(57) ABSTRACT

A terahertz image matrix sensor including a matrix of pixels and comprising, for each pixel, an antenna for receiving a terahertz radiation modulated by a signal at a modulation frequency and a synchronous filter with N pathways, where N is an integer greater than or equal to 4, each pathway including a capacitive element and at least one first breaker controlled by a first signal at said modulation frequency.

12 Claims, 3 Drawing Sheets

(51) Int. Cl.
  *G01S 17/89* (2006.01)
  *G01S 7/03* (2006.01)
  *G01S 7/491* (2006.01)
  *G01S 13/89* (2006.01)
  *G01V 8/00* (2006.01)
  *G01S 13/88* (2006.01)
  *H03H 19/00* (2006.01)

(52) U.S. Cl.
  CPC ............. *G01S 17/89* (2013.01); *G01S 13/887* (2013.01); *G01V 8/005* (2013.01); *H03H 19/002* (2013.01)

(56) References Cited

U.S. PATENT DOCUMENTS

| | | | |
|---|---|---|---|
| 5,432,517 A | 7/1995 | Billaud et al. | |
| 2005/0040909 A1* | 2/2005 | Waight | H03H 7/0153 333/17.1 |
| 2015/0365611 A1* | 12/2015 | Sekiguchi | G01S 17/89 250/208.1 |

OTHER PUBLICATIONS

International Search Report, dated Dec. 1, 2014, from corresponding International Application No. PCT/FR2014/052292.

Von Guinigen et al.: "An Integrated CMOS Switch-Capacitator Bandpass Filter Based on N-Path and Frequency-Sampling Principles," (1983) IEE Journal of Solid State Circuits; pp. 753-761.

Schuster et al: "A broadband THz imager in a low-cost CMOS technology," (2011) IEEE International Solid-State Circuits Conference; pp. 42-43.

Komachi & Tanaka: Lock-in amplifier using a sampled-datea synchronous filter,: (1974) J. Phys. E: Sci. Instrum.; pp. 967-971.

"Analog Switches and their application," (1980) Siliconix; Chapter 5: N-path Filters; pp. 5.1-5.12.

* cited by examiner

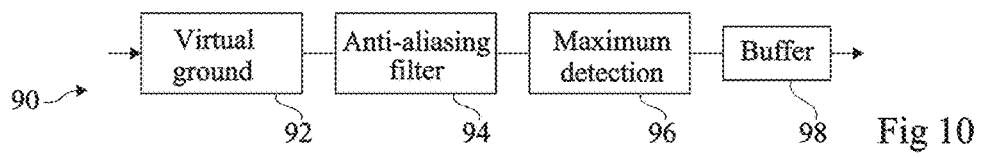
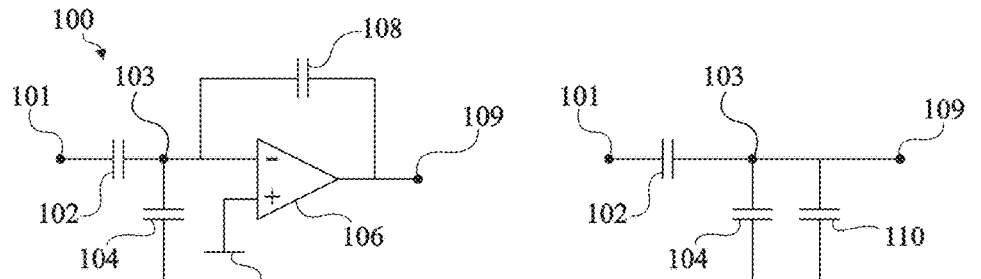
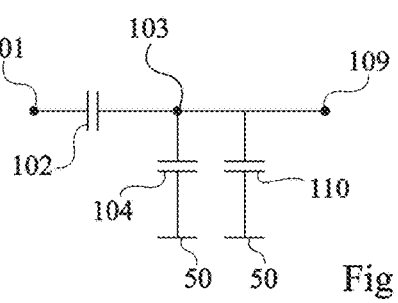
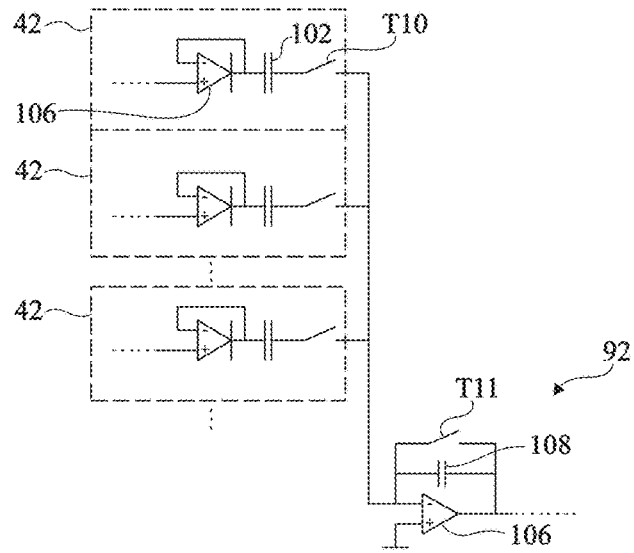
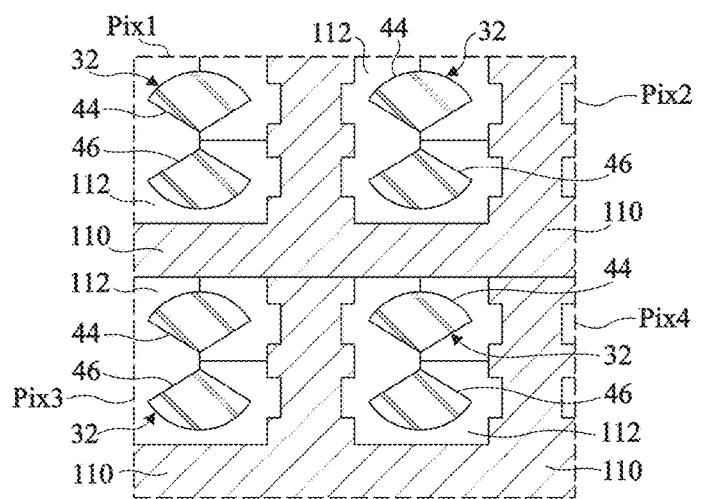

TERAHERTZ IMAGE SENSOR

CROSS-REFERENCE TO RELATED APPLICATIONS

This application is the national phase of International Application No. PCT/FR2014/052292, titled, filed on Sep. 15, 2014, which claims the priority benefit of French Application No. 13/59818, filed on Sep. 17, 2013, which applications are hereby incorporated by reference to the maximum extent allowable by law.

BACKGROUND

The present application relates to terahertz image sensors.

DISCUSSION OF THE RELATED ART

The field of terahertz frequencies approximately extends from 100 GHz to 30 THz, which corresponds to wavelengths varying from 0.01 mm to 3 mm.

Terahertz radiations have a strong penetrating power. They enable to see through many non-conductive materials, such as the skin, clothes, paper, wood, cardboard, plastics, etc. Such radiations have a low energy and are non-ionizing, which makes them relatively harmless and, in particular, enables them to be used in the medical and security fields.

Terahertz radiations may be used in many applications, especially in the field of high-speed telecommunications, wireless networks, radars, environmental monitoring, biomedical tests, the characterization of materials, gas or contaminant detection, counter-terrorism, astronomic observation, etc.

A significant research effort is currently conducted to develop terahertz sources and detectors, in particular to develop low-cost terahertz array image sensors.

SUMMARY

An embodiment provides a terahertz array image sensor comprising an array of pixels and comprising, for each pixel, an antenna for receiving a terahertz radiation modulated by a signal at a modulation frequency and an N-path synchronous filter, where N is an integer greater than or equal to 4, each path comprising a capacitive element and at least a first switch controlled by a first signal at said modulation frequency.

According to an embodiment, each path further comprises a first resistive element.

According to an embodiment, each path comprises the first switch in series with the capacitive element, a plurality of paths being arranged in parallel between a first node and a source of a reference potential.

According to an embodiment, the synchronous filter further comprises a second resistive element connected to the first node.

According to an embodiment, the second resistive element is formed by a switched-capacitance circuit.

According to an embodiment, the sensor comprises:

a first set of N/2 paths, the paths of the first set being arranged in parallel between the first node and the source of the reference potential;

a second switch between a second node and the first node and a third switch between the first node and a third node;

a second set of N/2 paths, the paths of the second set being arranged in parallel between a fourth node and the source of the reference potential; and a fourth switch between the second node and the fourth node and a fifth switch between the fourth node and the third node.

According to an embodiment, the sensor comprises a circuit for controlling the second and third switches with a second signal and the fourth and fifth switches with a third signal, the second and third signals being at the modulation frequency and being non-overlapping.

According to an embodiment, the sensor is made in integrated fashion.

According to an embodiment, the modulation frequency is in the range from 10 kHz to 1 MHz.

According to an embodiment, the sensor comprises, for each pixel, a detector capable of delivering a signal representative of the modulated radiation and at least one amplifier receiving the representative signal and capable of delivering an amplified signal, the synchronous filter receiving the amplified signal.

According to an embodiment, the radiation, in the absence of a modulation, has a frequency in the range from 100 GHz to 30 THz.

An embodiment also provides a system of terahertz imaging of an object, comprising:

a source of a terahertz radiation modulated by a signal at a modulation frequency; and a sensor of the modulated terahertz radiation returned by the object such as previously defined.

BRIEF DESCRIPTION OF THE DRAWINGS

The foregoing and other features and advantages will be discussed in detail in the following non-limiting description of specific embodiments in connection with the accompanying drawings, among which:

FIG. 10 shows, in the form of a block diagram, an embodiment of another portion of the terahertz image sensor of the imaging device of FIG. 1;

FIGS. 11 and 12 illustrate the operating principle of a virtual ground circuit;

FIG. 13 shows an embodiment of the virtual ground circuit of the image sensor of FIG. 10; and FIG. 14 is a partial simplified top view of an integrated embodiment of a terahertz image sensor.

DETAILED DESCRIPTION

Figure 1:
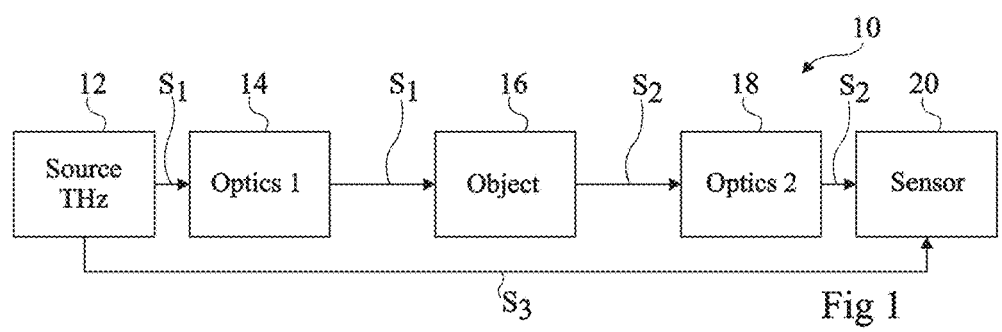
FIG. 1 shows in the form of a block diagram an embodiment of a terahertz imaging device.

For clarity, the same elements have been designated with the same reference numerals in the various drawings and, further, the various drawings are not to scale. In the following description, unless otherwise indicated, terms "substantially", "approximately", and "in the order of" mean "to within 10%". Further, only those elements which are useful to the understanding of the present description have been shown and will be described. In particular, the processing of the signals provided by an array image sensor, particularly for the display of an image, is well known by those skilled in the art and has not been described in further detail.

The signals likely to be measured by a terahertz radiation sensor generally have a low amplitude, close to that of noise. A processing of these signals should thus be implemented to extract the useful signal from the noise. It could be envisaged to implement a synchronous detection method where the terahertz radiation emitted by the radiation source is modulated by a carrier signal and where the useful signal is extracted from the measured signal by multiplying the measured signal by a control signal at the frequency of the carrier signal.

However, the inventors have shown that such a synchronous demodulation method cannot be implemented to form a terahertz array image sensor of decreased cost, and in particular formed in integrated fashion. Indeed, the multiplication step requires for the control signal by which the measured signal is multiplied to be in phase with the measured signal. This cannot be simply obtained with an array image sensor.

An array image sensor is formed of an array of pixels, a pixel corresponding to a site of the sensor, sensitive to terahertz radiation and having the smallest dimensions. The pixel dimensions define the spatial resolution of the obtained terahertz image. Since the signal detected by a pixel has a very low amplitude, the sensor comprises, for each pixel, an amplification device for example comprising a low-noise preamplifier, which receives the signal provided by the detector of the terahertz radiation, followed by a variable-gain amplifier.

However, the amplification of the detected signal may cause a phase shift which depends on the selected amplification gain and which may, further, vary from one pixel to the other for a same amplification gain. It cannot be envisaged, to form a terahertz image sensor of decreased cost, to correct the phase of the control signal each time the amplification gain changes and for each pixel.

The present invention provides modulating the terahertz radiation emitted by the radiation source with a carrier signal and filtering the measured signal at the frequency of the carrier signal with a highly-selective bandpass filter.

FIG. 1 shows in the form of a block diagram an embodiment of a terahertz imaging device 10.

Device 10 comprises a source 12 (THz Source) of a terahertz radiation, for example, at a frequency in the range from 100 GHz to 30 THz. The terahertz radiation is modulated, for example, by amplitude modulation, by a carrier signal at a modulation frequency f0 in the range from 10 kHz to 1 MHz, preferably in the range from 10 kHz to 500 kHz, more preferably from 10 kHz to 200 kHz, for example, approximately 100 kHz. Modulated radiation S1 is guided by an optical system 14 (Optics 1) all the way to an object 14 (Object) to be analyzed. Radiation S2 returned by object 16 is guided by an optical system 18 (Optics 2) all the way to a terahertz image sensor 20 (Sensor). Sensor 20 may, further, receive a signal S3 at frequency f0 provided by source 12.

Figure 2:
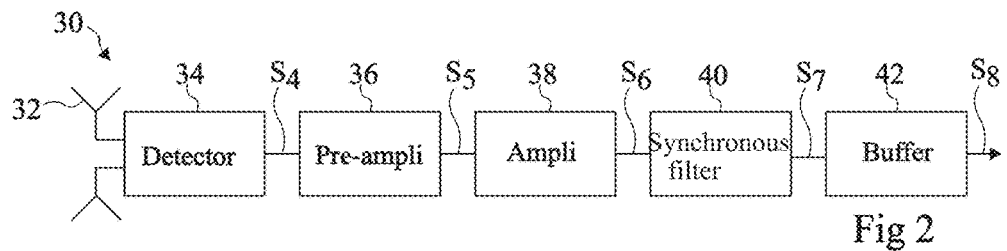
FIG. 2 shows, in the form of a block diagram, an embodiment of a portion of the terahertz image sensor of the imaging device of FIG. 1.

FIG. 2 shows, in the form of a block diagram, an embodiment of a circuit 30 corresponding to a portion of sensor 20. Circuit 30 is provided for each pixel of image sensor 20. The circuit 30 of each pixel comprises an antenna 32, receiving modulated terahertz radiation S2, connected to a detector 34 (Detector). Detector 34 delivers a signal 34 which comprises a useful signal, representative of the modulated terahertz radiation which has been measured, lost in noise. Signal S4 is a signal which may have an amplitude for example varying from a few microvolts to a few millivolts according to the exposure of sensor 20. Signal S4 should be amplified. This may be achieved by a plurality of successive amplification stages. As an example, circuit 30 comprises a low-noise preamplifier 36 (Pre-ampli) receiving signal S4 and delivering a signal S5 to a variable-gain amplifier 38 (Ampli). Amplifier 38 delivers a signal S6 to a synchronous filter 40 (Synchronous filter). Synchronous filter 40 delivers a signal S7 to an adapter circuit 42 (Buffer). Adapter circuit 42 delivers a signal S8 to a circuit described hereafter, which may be common to a plurality of pixels of sensor 20.

Figure 3:
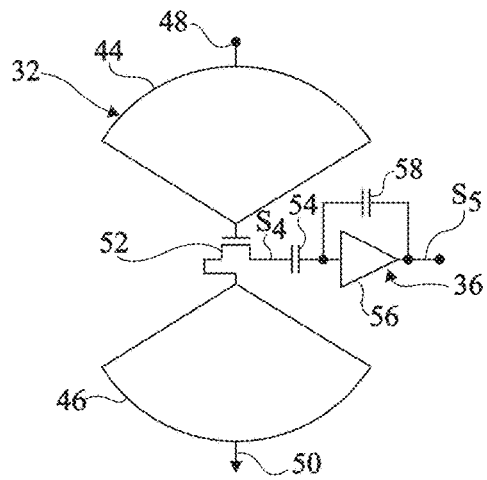
FIG. 3 schematically shows the antenna, the detector, and the preamplifier of the image sensor of FIG. 2.

FIG. 3 shows an embodiment of antenna 32, of detector 34, and of preamplifier 36. Antenna 32 may comprise two angular sectors 44, 46 of a conductive material, for example, two metallic angular sectors. The circular edge of angular sector 44 is connected to a source 48 of a high reference potential. The circular edge of angular sector 46 is connected to a source 50 of a low reference potential, for example, the ground of circuit 30. Detector 34 may correspond to a field-effect transistor, for example, a MOS transistor. The source of transistor 52 is connected to the top of angular sector 46. The drain of transistor 52 delivers signal S4 and is connected to the input of preamplifier 36. The gate of transistor 52 is connected to the top of angular sector 44. According to the present embodiment, preamplifier 36 comprises a capacitor 54 having an electrode receiving signal S4 and having its other electrode connected to the input of an amplifier 56 having its output delivering signal S5. Preamplifier 36 comprises an additional capacitor 58 having one electrode connected to the input of amplifier 56 and having its other electrode connected to the output of amplifier 56. The amplification gain of preamplifier 36 may be greater than or equal to 10, preferably greater than or equal to 20. Due to its operation, preamplifier 56 may further play the role of a low-pass filter and block frequencies greater than a few megahertz.

Amplifier 38 may perform an amplification, with an amplification gain which may take a plurality of discrete values between 1 and 100. As an example, amplifier 38 may comprise a plurality of amplification stages, for example, three amplification stages. Each amplification stage may comprise a transconductance amplifier and capacitors, where at least one of the capacitors may be shorted to modify the amplification gain of the stage.

Synchronous filter 40 receiving signal S6 is a narrow-band low-pass filter centered on modulation frequency f0 to suppress the noise outside of this frequency. Synchronous filter 40 is an N-path filter, each path comprising a capacitive element to be switched, and where N is an integer greater than or equal to 3. Preferably, N is a power of 2, such as 4, 8, 16, 32, etc. Synchronous filter 40 is controlled by a control signal S9, which is a clock signal at frequency N*f0. As a variation, it is possible for sensor 20 not to receive signal S3 delivered by source 12 and for sensor 20 to comprise a circuit for delivering signal S9. Advantageously, synchronous filter 40 operates independently from the phase shift between signal S6 and control signal S9.

Figure 4:
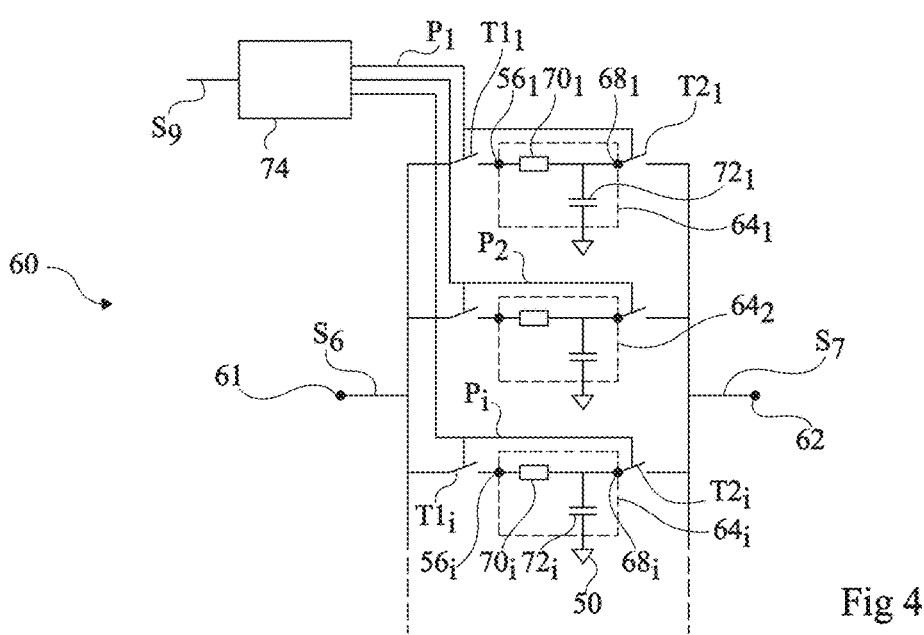
FIG. 4 shows an embodiment of the synchronous filter of the image sensor of FIG. 2.

FIG. 4 shows an embodiment of a circuit 60 capable of corresponding to synchronous filter 40 of FIG. 2. Filter 60 comprises an input node 61 receiving signal S6 and an output node 62 delivering signal S7. Filter 60 comprises N elementary filters 64$i$, with i varying from 1 to N. Each elementary filter 64$i$ comprises an input node 66$i$ and an output node 68$i$. Input node 66$i$ is connected to node 61 by a first switch T1$i$ and output node 68$i$ is connected to node 62 by a second switch T2$i$. Switches T1$i$ and T2$i$ may be formed of MOS transistors.

Each elementary filter 64$i$ may correspond to a low-pass filter comprising, as an example, a resistive element 70$i$ between nodes 66$i$ and 68$i$ and a capacitive element 72$i$ having an electrode connected to node 68$i$ and having its other electrode connected to source 50 of the low reference potential. All resistive elements 70$i$ may have the same resistance value R and all capacitive elements 72$i$ may have the same capacitance C. Resistive element means an element which has a resistive behavior and capacitive element means an element which has a capacitive behavior. Each resistive element may correspond to a resistor and each capacitive element may correspond to a capacitor.

Switches T1$i$ and T2$i$ are controlled by a signal Pi. Signals Pi, with i varying from 1 to N, are delivered by a circuit 74 receiving signal S9. Signals Pi are for example binary signals alternating between a "high" state and a "low" state. As an example, each switch T1$i$ and T2$i$ is off when signal Pi is in the low state and is on when signal Pi is in the high state. Signals Pi are non-overlapping, that is, when a signal Pi is in the high state, all the other signals Pj, with j different from are in the low state. As an example, circuit 74 comprises a counter, a decoder, and anti-overlap flip-flops.

Figure 5:
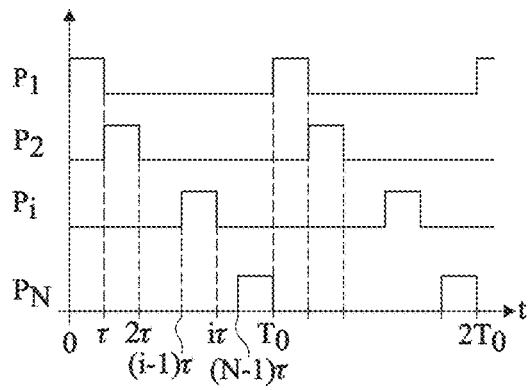
FIG. 5 is a timing diagram of control signals of the filter of FIG. 4.

FIG. 5 shows an example of timing diagram of signals Pi. Signals Pi are periodic binary signals having a period T0 equal to 1/f0. As an example, signal P1 is in the high state between times 0 and τ and then in the low state until time T0, where τ is substantially equal to T0/N. Signal P2 is in the low state between times 0 and τ and then in the high state between times τ and 2τ, and then again in the low state until time T0+τ. Signal Pi is in the low state between times 0 and (i−1)τ and then in the high state during time period τ, and then again in the low state until time T0+(i−1)τ. Signal PN is in the low state between times 0 and (N−1)τ and then at state 0 during time period τ, and then again in the low state until time T0+(N−1)τ.

Each elementary filter 64$i$ is thus cyclically scanned for a time period τ by signal S6. The time constant of low-pass filter 64$i$ is selected to be large as compared with switching period T0. A low-pass-to-high-pass transformation is then obtained due to the cyclic scanning.

The operating principle of synchronous filter 60 is the following. If signal S6 corresponds to a sinusoidal signal with a frequency equal to f0, each capacitor 72$i$ is then used, for each period T0, by the same portion of signal S6 which returns for each cycle. During an initialization phase, capacitor 72$i$ charges a little during time interval T0/N of the cycle and holds this charge for the rest of the time. In steady state, the voltage across capacitor 72$i$ has reached the average value of signal S6 at which it is used. One obtains on output node 62 the approximate shape of input signal S6 sampled by discrete values regularly distributed in the form of steps.

Figure 6:
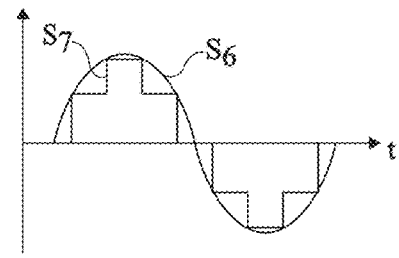
FIG. 6 shows curves of the variation of an input signal and of an output signal of the synchronous filter of FIG. 4.

FIG. 6 shows an example of curves of variation of signals S6 and S7 provided by synchronous filter 60 in the case where signal S6 corresponds to a sinusoidal signal of frequency f0.

When the frequency of input signal S6 differs from frequency f0, each capacitor 72$i$ is used by a value of input signal S6 which progressively shifts from one cycle to the other and successively takes all the values of the sinusoid. If the difference is large, capacitors 72$i$ cannot accumulate a significant charge and the voltage across each capacitor 72$i$ tends towards a zero average value. For sensor 20, signal S6 corresponds to the useful signal lost in noise. Signal S7 then corresponds to the line of signal S6 at frequency f0.

Figure 7:
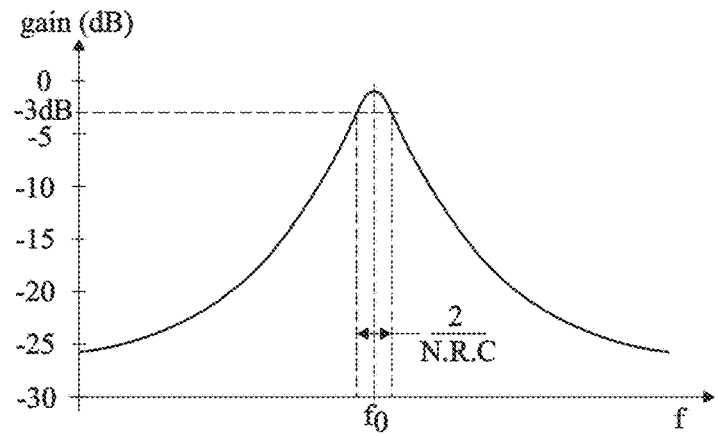
FIG. 7 shows an example of a curve of variation of the gain of the synchronous filter of FIG. 4.

FIG. 7 shows an example of a curve of variation of the gain of the synchronous filter 60 according to frequency. The transfer function of the filter is symmetrical with respect to frequency f0. Figure of merit Q of filter 60 depends on values R and C and on number N of paths. It is equal to 2/(NRC). Figure of merit Q is greater than or equal to 100, preferably greater than or equal to 300, more preferably greater than or equal to 500. The variation speed of the voltage across each capacitor 72$i$ varies according to the time constant of elementary low-pass filter 64$i$, that is, to product RC. Filter 60 is thus all the slower as it is selective.

By changing switching frequency N*f0, it is possible to modify central frequency f0 of the bandpass filter without changing the bandwidth. In addition to the response of the bandpass filter centered on frequency f0, filter 60 generates a series of lines centered on the harmonics of f0 and on the zero frequency. Since the filter samples at clock frequency N*f0, spectrum aliasing problems may be solved by limiting by anti-aliasing the input spectrum to a frequency lower than N*f0/2.

Figure 8:
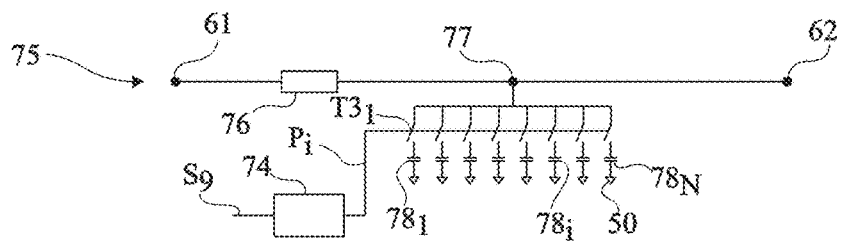
FIGS. 8 and 9 show other embodiments of the filter of the image sensor of FIG. 2.

FIG. 8 shows another embodiment of a synchronous N-path filter 75 capable of being used to form filter 40 of FIG. 2. Filter 75 comprises a resistive element 76 between node 61 and an intermediate node 77 connected to node 62. Filter 75 comprises N parallel paths, each path comprising a capacitor 78$i$ and a switch T3$i$. One electrode of capacitor 78$i$ is connected to source 50 of the low reference potential and the other electrode is connected to a terminal of switch T3$i$, the other terminal of switch T3$i$ being connected to node 77. Each switch T3$i$ is controlled by signal Pi delivered by circuit 74. Resistive element 76 has the value of resistance R and each capacitor 78$i$ has capacitance C. Filter 75 operates in the same way as previously-described filter 60. As compared with filter 60, filter 75 has the advantage that resistive element 76 is placed in common for the N paths of the filter and that the number of switches is decreased.

Figure 9:
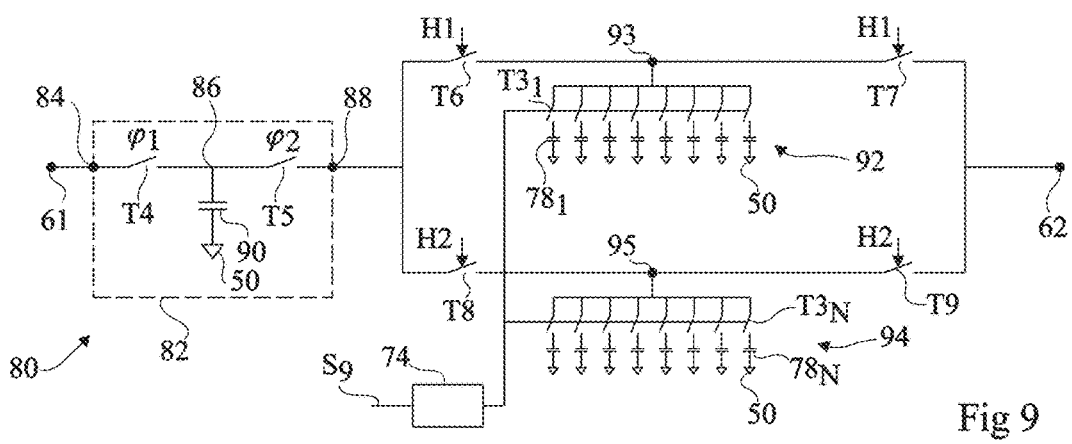

FIG. 9 shows another embodiment of an N-path synchronous filter 80 capable of being used to form filter 40 of FIG. 2. As compared with filter 75, resistive element 76 is formed by a switched capacitance circuit 82 comprising an input node 84 connected to node 61, an intermediate node 86, and an output node 88. Circuit 82 comprises a switch T4 controlled by a signal φ1 between input node 84 and intermediate node 86 and a switch T5 controlled by a binary signal φ2 between intermediate node 86 and output node 88. Circuit 82 further comprises a capacitor 90 between intermediate node 86 and source 50 of the low reference potential. Signals φ1 and φ2 are non-overlapping and are binary signals of frequency f1. Frequency f1 is greater than frequency f0. Preferably, frequency f1 is a multiple of frequency f0 to avoid parasitic intermodulation phenomena. The value of the equivalent resistance is R=1/C90f1 where C90 is the capacitance of capacitor 90.

As compared with filter 75, the N paths each comprising capacitor 78$i$ and switch T3$i$ are distributed in two subsets 92 and 94, each comprising N/2 paths. The N/2 paths of subset 92 are provided in parallel between a node 93 and source 50 of the low reference potential and the N/2 paths of subset 94 are provided in parallel between a node 95 and source 50 of the low reference potential. Filter 80 further comprises a switch T6 between node 88 and node 93 and a switch T7 between node 93 and output node 62. Switches T6 and T7 are controlled by a binary signal H1. Filter 80 further comprises a switch T8 between node 88 and node 95 and a switch T9 between node 95 and output node 62. Switches T8 and T9 are controlled by a binary signal H2. Signals H1 and H2 are non-overlapping and have periods T0. As an example, the duty cycle of each signal H1 and H2 is slightly smaller than ½. The fact of providing two sets of N/2 capacitors 78i enables to decrease the stray capacitances seen from node 88.

FIG. 10 shows, in the form of a block diagram, a circuit 90 corresponding to another portion of sensor 20 of FIG. 1. Circuit 90 may be common for a set of pixels of sensor 20, for example, for the pixels of a same pixel column. In this case, circuit 90 is repeated for each pixel column of sensor 20.

Circuit 90 successively comprises a virtual ground circuit 92 (Virtual ground), an anti-aliasing filter 94 (Anti-aliasing filter), a maximum detection circuit 96 (Maximum detection), and an adapter circuit 98 (Buffer).

Virtual ground circuit 92 is connected to the output of adapter circuit 42 associated with each pixel of a set of pixels, for example, with each pixel of a same pixel column of sensor 20. Circuit 92 enables to do away with the stray capacitance of the row connected to all the column pixels.

FIG. 11 shows a circuit 100 illustrating the operating principle of a virtual ground. It shows a capacitor 102 between a node 101 and a node 103, a capacitor 104 between node 103 and source 50 of the low reference potential, a transconductance amplifier 106 having its inverting input (−) connected to node 103 and having its non-inverting input (+) connected to source 50 of the low reference potential. A capacitor 108 is connected between node 103 and a node 109 which corresponds to the output of amplifier 106. In operation, circuit 100 is equivalent to the circuit shown in FIG. 12 where capacitor 108 and amplifier 106 are replaced with a capacitor 110 connected between node 103 and low reference potential source 50. The capacitance of capacitor 110 is equal to the product of the open-loop gain of amplifier 106 and of the capacitance of capacitor 108. If this product is greater than the capacitance of capacitor 104, the effects due to capacitor 104 are negligible.

In the present embodiment, capacitor 104 is representative of the stray capacitance of the row connected to the adapter circuits 42 of the pixels of a column of the pixel array and capacitor 102 is a capacitor of adapter circuit 42. The capacitance of capacitors 102 and 108 is substantially equal, so as to obtain a gain equal to 1 in absolute value.

FIG. 13 shows an embodiment of virtual ground circuit 92. Adapter circuit 42 of each pixel is schematically shown by a transconductance amplifier 106 assembled as a unity gain follower followed by capacitor 102 and by a switch T10. Virtual ground circuit 92 comprises transconductance amplifier 106 and capacitor 108. It may further comprise a switch T11 assembled in parallel with capacitor 108. In operation, the switches are successively turned on one after the others to successively connect each pixel to circuit 92. Virtual ground circuit 92 further has the advantage of attenuating the signals on the bus. Thus, the influence of the sinusoidal signals transmitted over the buses on the neighboring pixels is decreased.

Anti-aliasing filter 94 may comprise a continuous-time low-pass filter having a cut-off frequency greater than frequency f0. It enables to suppress the lines at the harmonics of frequency f0.

Adapter circuit 98 may have a structure similar to that of adapter circuit 42. The signals provided by adapter circuit 98 may be used, in particular, to display images on a display screen.

Maximum detection circuit 96 may comprise a sampling circuit.

FIG. 14 schematically shows a top view of four adjacent pixels Pix1, Pix2, Pix3, and Pix4 of a sensor 20 made in integrated fashion, for example, according to a CMOS technology. FIG. 14 is not drawn to scale. For each pixel Pix1, Pix2, Pix3, and Pix4, angular sectors 44 and 46 of antenna 32 have been shown, and a hatched area 110 shows the locations where the MOS transistors and the capacitors of circuit 30 are formed. Each capacitor 72i, 78i, may correspond to a metal-insulator-semiconductor capacitance or MOS capacitance and capacitor 90 may be formed by a metal-insulator-metal capacitance or MIM capacitance.

For each pixel Pix1, Pix2, Pix3, and Pix4, a free area 112 is provided around each antenna 32 to decrease the influence of circuit 30 on the measured radiation and the influence of the received radiation on circuit 30. Free area 112 does not comprise electronic components, except for detector 12, possibly preamplifier 36, the tracks for biasing antenna 23, and the track connecting preamplifier 36 to amplifier 38.

Examples of values of the components of circuits 30 and 90 are the following:

capacitance of capacitor 54: between 1 pF and 10 pF, for example, approximately 3 pF;

capacitance of capacitor 58: between 10 fF and 200 fF, for example, approximately 62 fF;

dimensions of each pixel: square surface having a side length in the range from 100 μm to 500 μm, for example, approximately 200 μm;

radius of each angular sector 44, 46: between 20 μm and 100 μm, for example, approximately 60 μm;

angle at the top of each angular sector 44, 46: between 90° and 180°, for example, approximately 120°;

capacitance of capacitor 90: between 2 pF and 20 pF, for example, approximately 10 pF;

frequency f1: between 100 kHz and 10 MHz, for example, approximately 1.6 MHz; and capacitance of each capacitor 78i: between 5 fF and 100 fF, for example, approximately 27 fF.

The equivalent resistance of circuit 82 is approximately 23 megohms. For a number N of paths equal to 16, synchronous filter 80 obtained with the specific previously-indicated values is a low-pass filter centered on frequency f0 having a selectivity factor in the order of 650.

Specific embodiments have been described. Various alterations and modifications will occur to those skilled in the art. In particular, although an embodiment of antenna 32 has been described where antenna 32 comprises two angular sectors 44, 46, the shape of antenna 32 may be different.

The invention claimed is:

1. A terahertz array image sensor comprising an array of pixels and comprising, for each pixel, an antenna for receiving a terahertz radiation modulated by a signal at a modulation frequency and an N-path synchronous filter, where N is an integer greater than or equal to 4, each path comprising a capacitive element and at least a first switch controlled by a first signal at said modulation frequency.

2. The sensor of claim 1, wherein each path further comprises a first resistive element.

3. The sensor of claim 1, wherein each path comprises the first switch in series with the capacitive element, a plurality of paths being arranged in parallel between a first node and a source of a reference potential.

4. The sensor of claim 3, wherein the synchronous filter further comprises a second resistive element connected to the first node.

5. The sensor of claim 4, wherein the second resistive element is formed by a switched-capacitance circuit.

6. The sensor of claim 4, comprising:
- a first set of N/2 paths, the paths of the first set being arranged in parallel between the first node and the source of the reference potential;
- a second switch between a second node and the first node and a third switch between the first node and a third node;
- a second set of N/2 paths, the paths of the second set being arranged in parallel between a fourth node and the source of the reference potential; and
- a fourth switch between the second node and the fourth node and a fifth switch between the fourth node and the third node.

7. The sensor of claim 6, comprising a circuit for controlling the second and third switches with a second signal and the fourth and fifth switches with a third signal, the second and third signals being at the modulation frequency and being non-overlapping.

8. The sensor of claim 1, characterized in that it is formed in integrated fashion.

9. The sensor of claim 1, wherein the modulation frequency is in the range from 10 kHz to 1 MHz.

10. The sensor of claim 1, comprising, for each pixel, a detector capable of delivering a signal representative of the modulated radiation and at least one amplifier receiving the representative signal and capable of delivering an amplified signal, the synchronous filter receiving the amplified signal.

11. The sensor of claim 1, wherein the radiation, in the absence of a modulation, has a frequency in the range from 100 GHz to 30 THz.

12. A system of terahertz imaging of an object, the system comprising:
- a source of a terahertz radiation modulated by a signal at a modulation frequency; and
- the sensor of the modulated terahertz radiation returned by the object of claim 1.

* * * * *